United States Patent
Horning et al.

(10) Patent No.: US 10,094,823 B2
(45) Date of Patent: Oct. 9, 2018

(54) PHOTOTHERMAL SPECTROSCOPY ASSAY READERS, AND RELATED ASSAY KITS AND METHODS

(71) Applicant: Tokitae LLC, Bellevue, WA (US)

(72) Inventors: Matthew P. Horning, Redmond, WA (US); Kevin Paul Flood Nichols, Issaquah, WA (US); Benjamin K. Wilson, Kirkland, WA (US)

(73) Assignee: TOKITAE LLC, Bellevue, WA (US)

( * ) Notice: Subject to any disclaimer, the term of this patent is extended or adjusted under 35 U.S.C. 154(b) by 76 days.

(21) Appl. No.: 14/604,396

(22) Filed: Jan. 23, 2015

(65) Prior Publication Data

US 2016/0216260 A1    Jul. 28, 2016

(51) Int. Cl.

| | |
|---|---|
| *G01N 21/00* | (2006.01) |
| *G01N 33/558* | (2006.01) |
| *G01N 33/543* | (2006.01) |
| *G01N 33/553* | (2006.01) |
| *G01N 21/17* | (2006.01) |
| *G01N 21/84* | (2006.01) |

(52) U.S. Cl.
CPC ......... *G01N 33/558* (2013.01); *G01N 21/171* (2013.01); *G01N 33/54346* (2013.01); *G01N 33/54386* (2013.01); *G01N 33/553* (2013.01); *G01N 21/8483* (2013.01); *G01N 2021/1714* (2013.01)

(58) Field of Classification Search
CPC .......... G01N 33/558; G01N 33/54393; G01N 33/54366; G01N 33/54346; G01N 33/54386; G01N 33/582; G01N 2035/00108; G01N 21/6428; G01N 21/658; G01N 21/8483; G01N 21/78; G01N 2201/06113; G01N 2201/068; G01N 2021/1714; G01N 21/171; G01N 33/553

See application file for complete search history.

(56) References Cited

U.S. PATENT DOCUMENTS

| | | |
|---|---|---|
| 4,496,839 A | 1/1985 | Bernstein et al. |
| 7,262,414 B1 | 8/2007 | Carrieri et al. |
| 2008/0018890 A1 | 1/2008 | Maity et al. |

(Continued)

FOREIGN PATENT DOCUMENTS

| | | |
|---|---|---|
| EP | 0 594 412 A1 | 4/1994 |
| EP | 2 743 688 A1 | 6/2014 |

(Continued)

OTHER PUBLICATIONS

Qin et al., "Significantly Improved Analytical Sensitivity of Lateral Flow Immunoassays by Thermal Contrast", Angew. Chem. Int. Ed. Engl., 2012, v, 51, No. 18, pp. 4358-4361.*

(Continued)

*Primary Examiner* — Xiaoyun R Xu

(74) *Attorney, Agent, or Firm* — Dorsey & Whitney LLP

(57) ABSTRACT

Embodiments disclosed herein are directed to a photothermal spectroscopy assay reader including a light source configured to emit light in the red range of the light spectrum. Methods of operating such photothermal spectroscopy assay readers are also disclosed. Assay kits including a lateral flow assay and a photothermal spectroscopy assay reader configured to read the photothermal spectroscopy assay reader are also disclosed.

29 Claims, 7 Drawing Sheets

(56) References Cited

U.S. PATENT DOCUMENTS

| | | | |
|---|---|---|---|
| 2010/0135857 | A1 | 6/2010 | Hunter et al. |
| 2012/0061587 | A1 | 3/2012 | Wu et al. |
| 2014/0170674 | A1 | 6/2014 | He |
| 2014/0377770 | A1 | 12/2014 | Bischof et al. |
| 2015/0036145 | A1 | 2/2015 | Cichos et al. |

FOREIGN PATENT DOCUMENTS

| | | |
|---|---|---|
| GB | 2 426 815 A | 12/2006 |
| WO | WO 2004/090512 A1 | 10/2004 |
| WO | WO 2013/116333 A2 | 8/2013 |
| WO | WO 2013/186735 A2 | 12/2013 |

OTHER PUBLICATIONS

Honda et al. In "Nanoscale heating of laser irradiated single gold nanoparticles in liquid", Optics Express, 2011,v. 19, No. 13, pp. 12375-12383.*

NanoAct, see http://www.dcndx.com/service-detail/development-using-nanoact-cellulose-nanobeads, pp. 1-2, no date.*

Dell in "Towards a Point-of-Care Diagnostic System: Automated Analysis of Immunoassay Test Data on a Cell Phone" NSDR, Jun. 28, 2011, pp. 3-8.*

"DCN Diagnostics and Asahi Kasei Fibers Corporation launch market collaboration on a new colored nanoparticle designed to increase sensitivity in rapid assays", Jul. 26, 2013, pp. 1-2.*

Stephen E. Bialkowski, "Photothermal Spectroscopy Methods for Chemical Analysis", vol. 134 "Chemical Analysis: A Series of Monographs on Analytical Chemistry and Its Applications" J. D. Winefordner, Series Editor 1996, John Wiley & Sons, Inc., pp. 1-44.*

Gemeiner et al., "Bead cellulose and its use in biochemistry and biotechnology", Chem. Papers, 1989, v.43, No. 6, pp. 805-848.*

Hans Boehringer, "Direct comparison of NanoAct™ cellulose particle versus colloidal gold particle based hCG lateral flow assays", Jun. 2013, pp. 1-3: http://www.dcndx.com/Upload/Product/635074074987731688.pdf.*

PCT International Search Report; International App. No. PCT/US2016/017678; dated May 11, 2016; pp. 1-3.

U.S. Appl. No. 14/630,489, Gasperino et al.

PCT International Search Report; International App. No. PCT/US2016/013883; dated Apr. 14, 2016; pp. 1-3.

European Patent Office, Supplementary European Search Report, Pursuant to Rule 62 EPC; App. No. EP 16740581; dated May 17, 2018; pp. 1-8.

European Patent Office, Supplementary European Search Report, Pursuant to Rule 62 EPC; App. No. EP 16756064; dated Jul. 17, 2018; pp. 1-8.

* cited by examiner

PHOTOTHERMAL SPECTROSCOPY ASSAY READERS, AND RELATED ASSAY KITS AND METHODS

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)).

PRIORITY APPLICATIONS

None.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

BACKGROUND

A lateral flow assay (LFA) can be a paper-based device that detects a presence of an analyte in a sample. LFAs are a common point of care diagnostic tool. LFAs can function by wicking (e.g., capillary action) a sample of interest through a porous membrane (e.g. paper) where chemical reactions can occur in and on the surface of the porous membrane.

The LFA can contain a conjugate material therein, which are typically formulated to provide a solvent(s) and reactant (s) necessary to dissolve, react, color, tag, or bond to the suspected analyte in a sample. Thus, if the analyte is present, the conjugate or a component thereof will react with the analyte in the sample. The conjugate can include a taggant or other material configured to provide a visual indication of the presence of the analyte, reacted analyte, or analyte-conjugate complex. Typically, the readout of an LFA is a visual change at some point along a length of the LFA. Many LFAs include an analyte collection material near a distal end of the LFA where the analyte and any taggant bonded thereto are bound in large concentration in a sample matrix to provide a visual indication of a positive or a negative result.

Photothermal spectroscopy assay readers can enhance the sensitivity of LFA results beyond visual detection. A photothermal spectroscopy assay reader directs light towards a surface of an LFA that can be saturated with the sample of interest. The conjugate material reacted with the analyte in the sample can absorb energy from the light. The photothermal spectroscopy assay reader can detect a thermal response from the surface of the LFA, which can provide an indication of the presence of the analyte.

Manufacturers and users of photothermal spectroscopy assay readers and LFAs continue to seek photothermal spectroscopy assay readers and LFAs with improved limits of detection.

SUMMARY

Embodiments disclosed herein are directed to photothermal spectroscopy assay readers for detecting a presence of an analyte in a sample introduced to an LFA and related assay kits. The photothermal spectroscopy assay readers disclosed herein include a light source configured to emit light in the red range of the light spectrum (e.g., about 600 nm to about 750 nm). Methods of operating such photothermal spectroscopy assay readers are also disclosed.

In an embodiment, a photothermal spectroscopy assay reader for detecting a presence of an analyte in a sample disposed in a lateral flow assay is disclosed. The photothermal spectroscopy assay reader includes a sample holder that is configured to receive an LFA including a test region therein. The photothermal spectroscopy assay reader includes a light source that is configured to emit light in the red range of the light spectrum to be received by the test region of the LFA. For example, the light source is configured to emit light exhibiting an average wavelength of about 600 nm to about 750 nm. The photothermal spectroscopy assay reader further includes a thermal sensor. The thermal sensor is configured and positioned to detect a thermal response from the test region of the LFA.

In an embodiment, a method of using a photothermal spectroscopy assay reader is disclosed. The method includes receiving one or more signals indicating that an LFA is present in a sample holder of the photothermal spectroscopy assay reader. The method includes emitting light from a light source that is received by a test region of the LFA. The light emitted by the light source is in the red range of the light spectrum. The method further includes, responsive to emitting the light, detecting a thermal response from the test region of the LFA with a thermal sensor.

In an embodiment, an assay kit is disclosed that includes a photothermal spectroscopy assay reader and an LFA. The LFA includes a sample pad configured to receive a fluid sample. The LFA includes a conjugate pad that includes a conjugate material. The conjugate material is configured to bind with a selected analyte. Additionally, the conjugate material is configured to absorb more energy from a light in the red range of the light spectrum than the sample when the LFA is exposed to the light. The LFA further includes a test region that contains a collection material. The collection material is configured to bind with the selected analyte bound to the conjugate material. The photothermal spectroscopy assay reader includes a sample holder that is configured to receive the LFA. The photothermal spectroscopy assay reader includes a light source that is configured to emit a light in the red range of the light spectrum to be received by the test region of the LFA. For example, the light source is configured to emit a light exhibiting a wavelength of about 600 nm to about 750 nm. The photothermal spectroscopy assay reader can further include a thermal sensor. The thermal sensor is positioned and configured to detect a thermal response from the test region of the LFA.

Features from any of the disclosed embodiments can be used in combination with one another, without limitation. In addition, other features and advantages of the present disclosure will become apparent to those of ordinary skill in the art through consideration of the following detailed description and the accompanying drawings.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
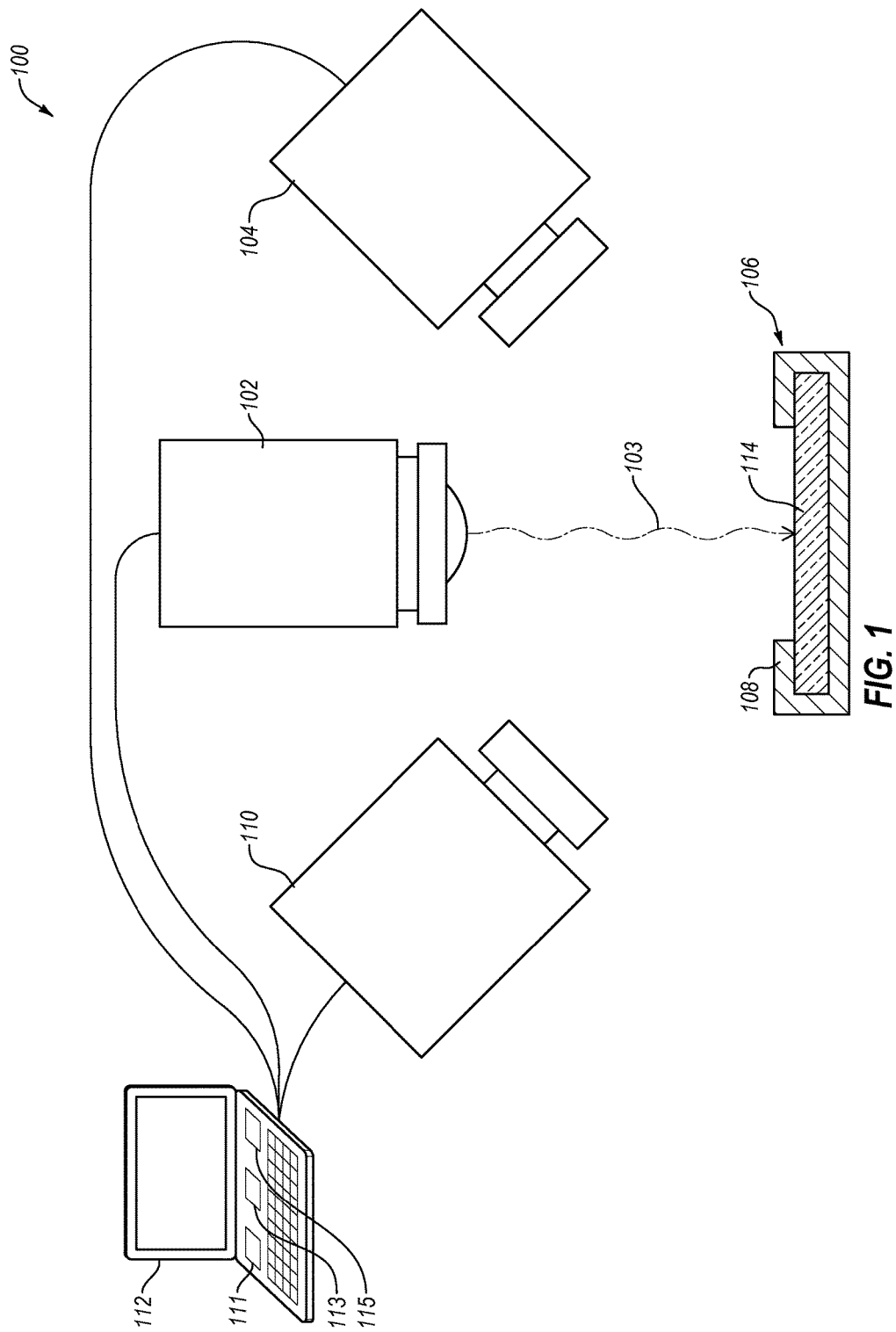
FIG. 1 is a schematic illustration of a photothermal spectroscopy assay reader according to an embodiment.

Embodiments disclosed herein are directed to photothermal spectroscopy assay readers for detecting a presence of an analyte in a sample introduced to an LFA and related assay kits. The photothermal spectroscopy assay readers disclosed herein include a light source configured to emit light in the red range of the light spectrum (e.g., about 600 nm to about 750 nm). Methods of operating such photothermal spectroscopy assay readers are also disclosed.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments can be utilized, and other changes can be made, without departing from the spirit or scope of the subject matter presented here.

Photothermal spectroscopy assay readers can be used to provide point of care testing for a variety of purposes, such as drug tests, pregnancy tests, flu tests, fertility tests, human immunodeficiency virus (HIV) tests, hepatitis tests, by way of non-limiting example. The photothermal spectroscopy assay readers can be configured to detect a presence of an analyte in a LFA. The LFAs function by receiving a sample (e.g., blood) that can contain an analyte and moving the sample through a length of the LFA via capillary action. During capillary transport, the analyte in the sample can be exposed to a conjugate material (e.g., 40 nm gold nanoparticles or other suitable conjugate material) configured to react with the analyte to aid in detection thereof. The capillary transport can move the sample including the analyte bonded to the conjugate material (i.e., the conjugated analyte), if present, to a test region of the LFA. The photothermal spectroscopy assay readers can be configured to emit light to be received by the test region of the LFA and detect a thermal response from the test region of the LFA responsive to receiving the light, which is indicative of the presence or lack of presence of the analyte.

The disclosed embodiments include a light source configured to emit light in the red range of the spectrum (e.g., about 600 nm to about 750 nm) directly or indirectly towards a test region of the LFA. The LFAs can include one or more conjugate materials that absorb light strongly in the red range of the light spectrum relative to other wavelengths. For example, the conjugate materials can include thermally-responsive indicator particles, such as at least one of at least one of blue cellulose nanobeads, silver nanoplates, silver nanoparticles, gold nanorods, gold nanocages, gold nanorods, gold nanocages, off-resonance gold nanospheres, multi-walled carbon nanotubes, carbon fullerenes, platinum nanoparticles, colloidal magnetite nanoparticles, ferrite nanoparticles, or conjugated dyes. The photothermal spectroscopy assay readers can be used with LFAs that use a blood sample and improve detection of low concentration analytes in the blood sample. For example, the analytes can include proteins associated with malaria parasites. The peak absorbance in the red range of the light spectrum is distinct from the absorbance of the blood and a top layer of the LFA. Therefore, the photothermal spectroscopy assay readers provide improved sensitivity over visual detection or use of another wavelength of light outside of the red range of the light spectrum.

FIG. 1 is a schematic illustration of a photothermal spectroscopy assay reader 100 according to an embodiment. The photothermal spectroscopy assay reader 100 is configured to detect a presence of one or more analytes in a sample within an LFA. The photothermal spectroscopy assay reader 100 includes a light source 102 that is configured to emit light 103 in the red range of the light spectrum. The light source 102 can be configured to emit light 103 having an average or dominant wavelength of about 600 nm to about 750 nm. The light source 102 is configured to emit the light 103 directly or indirectly towards a test region of an LFA 114 to be tested. The LFA 114 can be positioned on a sample holder 106. The photothermal spectroscopy assay reader 100 further includes a thermal sensor 110 configured to detect a thermal response from a surface of the LFA 114 responsive to being exposed to the light 103 from the light source 102. The photothermal spectroscopy assay reader 100 can analyze the detected thermal response or can output the detected thermal response to computer 112 operably connected to the photothermal spectroscopy assay reader 400.

The photothermal spectroscopy assay reader 100 can detect the presence of the one or more analytes in the sample by having the LFA 114 positioned on the sample holder 106. The LFA 114 can have a sample (e.g., blood) applied thereto and the sample can contain one or more analytes. After waiting sufficient time for the sample to transport through the LFA 114, the light source 102 emits the light 103 directly or indirectly towards the test region of the LFA 114. The test region of the LFA 114 can absorb or receive the light 103. The thermal sensor 110 detects the thermal response of the LFA 114 caused by the LFA 114 absorbing the light 103. The photothermal spectroscopy assay reader 100 is then configured to analyze the detected thermal response to determine if the sample contained the specific analyte therein.

The light source 102 is configured to emit the light 103 in the red range of the light spectrum. The red range of the light spectrum includes light exhibiting an average wavelength between about 600 nm to about 750 nm. For example, the average wavelength of light 103 can be about 600 nm to about 625 nm, about 625 nm to about 650 nm, about 650 nm to about 675 nm, about 675 nm to about 700 nm, about 700 nm to about 725 nm, or about 725 nm to about 750 nm. The light source 102 can be configured to emit light 103 at a single wavelength or multiple wavelengths. For example, the light source 102 can be selected to emit the light 103 at a specific selected average or selected dominant wavelength. In such an embodiment, the light source 102 can be removable such that a user can replace the current light source 102 with a light source that emits a light exhibiting a different dominant wavelength.

The light source 102 can be configured to emit the light 103 in order to improve the limit of detection of the photothermal spectroscopy assay reader 100. For example, the limit of detection can be related to an absorbance (i.e., the amount of energy from the light 103 absorbed) of the conjugate material, the sample matrix, and a top layer of the LFA 114. The absorbance of a material can be at least partially related to the wavelength of the light 103. The limits of detection can be improved when the absorbance of the conjugate material is increased relative to the absorbance of the sample matrix and the top layer of the LFA 114. For example, when the light source 102 is configured to emit the light 103 in the red range of the spectrum, the ratio of absorbance of the conjugate material to that of the sample can be greater than the same ratio when configured in the green range of the spectrum. For example, the light source 102 can be configured to emit the light 103 in the red range of the spectrum such that the absorbance of the conjugate material is about 1.25 times greater than the absorbance of the sample and the top layer of the LFA 114. In an embodiment, the light source 102 can be configured to emit the light 103 in the red range of the light spectrum such that the ratio of absorbance of the conjugate material to that of the sample and the top layer of the LFA is about 2 times greater, about 5 times greater, about 10 times greater or more than 10 times greater than the absorbance of the sample and the top layer of the LFA 114 in the green range of the spectrum. Therefore, the exact average or dominant wavelength emitted by the light source 102 can affect the limit of detection of the photothermal spectroscopy assay reader 100. Accordingly, the wavelength emitted by the light source 102 can be at least partially dependent on the materials present in the test region.

For example, the photothermal spectroscopy assay reader 100 can be configured to detect the presence of an analyte in a sample including blood, in particular, hemoglobin. The LFA 114 can contain a conjugate material including 40 nm gold nanoparticles. The conjugate material can be configured to bond to a selected analyte. At wavelengths lower than about 580 nm, gold nanoparticles having an average particle size of about 40 nm and hemoglobin both have peaks in their absorbance spectra. At wavelengths greater than about 575 nm, the absorbance of the 40 nm gold nanoparticles and hemoglobin begin to decrease. However, the absorbance of the hemoglobin decreases significantly faster than the 40 nm gold nanoparticles. At some concentrations of gold nanoparticles and hemoglobin, the relative absorbance of the 40 nm gold nanoparticles can be at least about 1.25 times greater than the absorbance of the hemoglobin. At the same concentrations, and at wavelengths of at about 650 nm, the relative absorbance of the 40 nm gold nanoparticles can be more than about 10 times greater than the absorbance of the hemoglobin. Therefore, the light source 102 can be configured to emit light 103 at an average wavelength greater than about 600 nm and, more particularly, at an average wavelength greater than about 650 nm. Such a configuration can improve the photothermal spectroscopy assay reader's 100 limits of detection even though the relative absorbance of both materials is significantly lower at these wavelengths.

The light source 102 can include any device configured to emit the light 103 in the red range of the light spectrum. The light source 102 can include one or more light emitting diodes (LED) light, a focused light source (e.g., a light focused using a parabolic mirror or lenses), a laser, or another light source. Additionally, the light source 102 can be configured to emit a continuous, oscillating, or pulsating light.

In an embodiment, the light source 102 can be a laser configured to emit a continuous laser beam in the red range of the light spectrum for a relatively insignificant duration. In an embodiment, the light source 102 can be a pulse laser configured to emit a laser beam in the red range of the light spectrum. The pulse laser can be configured to emit a laser beam about every 1 ms to about every 1000 ms, such as about 100 ms to about 500 ms, or about 500 ms to about 1000 ms. The time between pulses from the pulse laser can be selected to allow the test region of the LFA 114 to dissipate at least a portion of the absorbed energy between the pulses. Failure to sufficiently dissipate energy can degrade the sample, the conjugated analyte, or the thermal response.

In an embodiment, the photothermal spectroscopy assay reader 100 can be configured to emit the light 103 at a specific selected intensity. For example, a relatively high intensity light can degrade or damage the conjugated analyte, the sample, or the LFA 114. The relatively high intensity light can increase the noise detected by the photothermal spectroscopy assay reader 100. In an embodiment, the intensity of the emitted light 103 can be selected based on the LFA 114 used or the sample to be measured. For example, the LFA 114 can include a conjugate material including 40 nm gold nanoparticles. The absorbance of 40 nm gold nanoparticles is greater for a light exhibiting an average wavelength of about 600 nm than light exhibiting an average wavelength of about 650 nm. As such, the light source 102 can emit a relatively low intensity light having a wavelength of about 600 nm or a relatively high intensity light having an average wavelength of about 650 nm if the conjugate material includes 40 nm gold nanoparticles.

The light source 102 can be configured to emit a specific intensity of light based on the type of light source 102. In an embodiment, a continuous light source (e.g., a laser) can be configured to emit less intense light than a non-continuous light source (e.g., a pulsating light source). For example, when the light source 102 is a laser, the output power of the laser can be less than about 50 W (e.g., less than about 25 W, less than about 5 W, less than about 2.5 W, or less than about 1 W). In an embodiment, the light source 102 can be configured to emit a relatively less intense light when the light source 102 is configured to emit a focused light (e.g., a laser beam) than a non-focused light (e.g., an LED light source).

The light source 102 can be positioned to improve the limit of detection of the photothermal spectroscopy assay reader 100. For example, the light source 102 can be positioned such that the light 103 emitted by the light source 102 is directed towards the test region at an angle substantially perpendicular to a surface of the test region. Such a configuration can cause a limited surface area of the test region to absorb energy from the light source 102. The limited surface area exposed to the light 103 can increase the detected temperature gradient and enable the use of a less intense light. In an embodiment, the light source 102 can be positioned such that the light 103 emitted by the light source 102 is directed towards the test region at a non-perpendicular angle, such as about 10 degrees to about 60 degrees (e.g., about 45 degrees to about 50 degrees). Such a configuration can cause a larger surface area of the test region to absorb energy from the laser beam. The position of the light source 102 can be selected based on other considerations, such as space requirements and the positioning of other elements of the photothermal spectroscopy assay reader 100.

The photothermal spectroscopy assay reader 100 can include multiple ones of the light sources 102. In an embodiment, the photothermal spectroscopy assay reader 100 can include two light sources 102 that emit light 103 towards two separate regions or locations of the test region. For example, each light source 102 can be configured to emit light at different average wavelengths and/or intensities. Two or more light sources 102 can allow the photothermal spectroscopy assay reader 100 to test for two different analytes substantially simultaneously. In an embodiment, the two light sources 102 can be positioned and configured to emit light 103 at the same location or different locations. In some embodiments, two or more light sources can be selected to provide a greater ratio of absorbance differentiation between the sample matrix and the LFA than a single light source.

The photothermal spectroscopy assay reader 100 can further include a light sensor 104 configured to detect the light 103 emitted from the light source 102. The light sensor 104 can include any suitable device configured to detect the light 103 in the red range of the spectrum. For example the light sensor 104 can include an optical sensor (e.g., one or more photodiodes) or a camera. In some embodiments, the light sensor 104 can include infrared sensor arrays, such as a 2×2 or 10×10 sensor array. In some embodiments, the light sensor 104 can include a directional infrared (IR) sensor. In some embodiments, the light sensor 104 can include a scanning IR sensor. In some embodiments, the light sensor 104 can include a contact thermal sensor. The light sensor 104 can be configured to detect at least one of the intensity of the light 103, the oscillating/pulse rate of the light 103, or the surface area illuminated by the light 103. In an embodiment, the light sensor 104 can be used to calibrate the light source 102. In an embodiment, the light sensor 104 can be configured to allow a user to watch or otherwise visually observe the photothermal spectroscopy assay reader 100 test the LFA 114.

As previously discussed, the photothermal spectroscopy assay reader 100 can further include the sample holder 106 that is configured to receive the LFA 114. The sample holder 106 can be any suitable device configured to support the LFA 114. For example, the sample holder 106 can include a flat surface on which the LFA 114 can be placed. Additionally, the sample holder 106 can include a number of features. For example, the sample holder 106 can include a positioning feature 108 that can help position the LFA 114 on the sample holder 106. For example, the positioning feature 108 can include walls, brackets, channels, markings, or other suitable positioning features.

The sample holder 106 can be formed of a material that is configured to affect the thermal response of the LFA 114. In an embodiment, the sample holder 106 can be configured to affect the heat dissipation of the LFA 114. For example, the sample holder 106 can be formed of a material exhibiting a relatively high thermal conductivity that facilitates dissipation of heat absorbed by the test region to the sample holder 106. For example, the sample holder 106 can be formed from aluminum, aluminum alloys, copper, copper alloys such as brass or bronze, or other suitably thermally conductive material. Alternatively, the sample holder 106 can include a device, such as a heat sink or a heat pump (e.g., one or more Peltier cells), which dissipates heat from the test region of the LFA 114. In an embodiment, the sample holder 106 can be formed of a material exhibiting a low thermal conductivity that limits heat dissipation from the LFA 114 to the sample holder 106.

In an embodiment, the sample holder 106 can include one or more sensors (not shown) configured to detect a presence of the LFA 114 on the sample holder 106. In an embodiment, the sensor can be a weight sensor configured to detect a presence of the LFA 114 on the sample holder 106. In an embodiment, the sensor can be configured to determine a position of the LFA 114. The sensor can include an optical sensor, a mechanical sensor, or another suitable sensor configured to sense the presence or determine the position of the LFA 114. The sensor can be incorporated into the positioning feature 108 such that the sensor detects the LFA 114 when the LFA 114 is at least partially inserted into the positioning feature 108 (e.g., fully or partially inserted).

As previously discussed, the photothermal spectroscopy assay reader 100 further includes the thermal sensor 110, which is configured to detect a thermal response from the test region of the LFA 114 responsive to the LFA 114 being irradiated with light 103 from the light source 102. The thermal response can be a temperature gradient generated in the LFA 114. The thermal sensor 110 can include any device configured to detect the thermal response from the LFA 114 during or after the LFA 114 is exposed to the light 103 emitted by the light source 102. For example, the thermal sensor 110 can include an infrared camera, an infrared sensor, or another heat sensor. The thermal sensor 110 can have a resolution sufficient to detect the requisite temperature gradients in the LFA 114.

In some embodiments, the photothermal spectroscopy assay reader 100 can include two or more thermal sensors 110. In an embodiment, the two or more thermal sensors 110 can be configured to detect a thermal response from different regions or locations of the test region of the LFA 114. In an embodiment, the two or more thermal sensors 110 can be configured to detect a thermal response from a single location of the LFA 114. Such a configuration can improve the overall resolution of the thermal response or an increase the likelihood that at least one of the thermal sensors 110 detects the maximum temperature gradient. In an embodiment, one of the thermal sensors 110 can be configured to help a user calibrate the light source 102 and the other one of the thermal sensors 110 can be used during testing to detect the thermal response.

In an embodiment, the thermal sensor 110 can include internal electrical circuitry. For example, the thermal sensor 110 can include a microprocessor that operates in accordance with instructions stored in memory associated with the microprocessor. The microprocessor can be configured to at least partially analyze data from the detected thermal response. For example, the microprocessor can be configured to determine whether the sample contains an analyte.

In an embodiment, the thermal sensor 110 includes an output that outputs data about the detected thermal response. The thermal sensor 110 can output the data from the detected thermal response to another component, such as computer 112, either wirelessly or through a wired connection. In an embodiment, the thermal sensor 110 outputs data from the detected thermal response. For example, the thermal sensor 110 can output data via an analog-to-digital converter that is operably coupled to the computer 112. In an embodiment, the thermal sensor 110 outputs data that has been at least partially analyzed by the thermal sensor 110. In an embodiment, the at least partially analyzed data can be output directly to a user (e.g., output to a display).

The computer 112 of the photothermal spectroscopy assay reader 100 can include one or more processors 111 that operate in accordance to instructions stored in memory electrical circuitry 113 associated with the computer 112. For example, the computer 112 can be a desktop computer, a laptop computer, or a mobile device (e.g., a tablet or phone). The computer 112 can be communicably and operably coupled to every component of the photothermal spectroscopy assay reader 100. For example, the computer 112 can be communicably and operably coupled to at least one of the light source 102, the light sensor 104, the thermal sensor 110, or other components of the photothermal spectroscopy assay reader 100. The computer 112 can at least partially control one or more components of the photothermal spectroscopy assay reader 100.

In an embodiment, responsive to the sensor of the sample holder 106 detecting the presence of an LFA 114 thereon, the computer 112 causes the one or more processors 111 thereof to instruct the light source 102 to emit the light 103 at a specific dominant or average wavelength or intensity. For example, the computer 112 can include an input that allows a user to communicate the presence of the LFA 114 on the sample holder 106 to the computer 112. For example, the input can include a display, keyboard, manual input, audible input, or a digital input such as a USB or Ethernet connection or other input devices. For example, the user can instruct the computer 112 to execute a test that can be stored in the memory electrical circuitry 113 or can be inputted by the user.

The computer 112 can be located at least partially within, proximate to, or remote from the photothermal spectroscopy assay reader 100. For example, the computer 112 can be wirelessly or wiredly coupled to the components of the photothermal spectroscopy assay reader 100.

The computer 112 can also include diagnostic electrical circuitry 115. The diagnostic electrical circuitry 115 can include one or more processors operating in accordance with instructions stored in memory. Alternatively, the diagnostic electrical circuitry 115 can be incorporated with the one or more processors 111 and memory electrical circuitry 113 of the computer 112. The diagnostic electrical circuitry 115 can be operably coupled to the thermal sensor 110 or other components of the photothermal spectroscopy assay reader 100. For example, the diagnostic electrical circuitry 115 can be configured to receive data from the thermal sensor 110. The diagnostic electrical circuitry 115 can analyze the data to determine the diagnostic condition. The diagnostic condition can include an indication of the presence of the analyte within the sample. The diagnostic electrical circuitry 115 can be configured to output the diagnostic condition to a user.

Figure 2A:
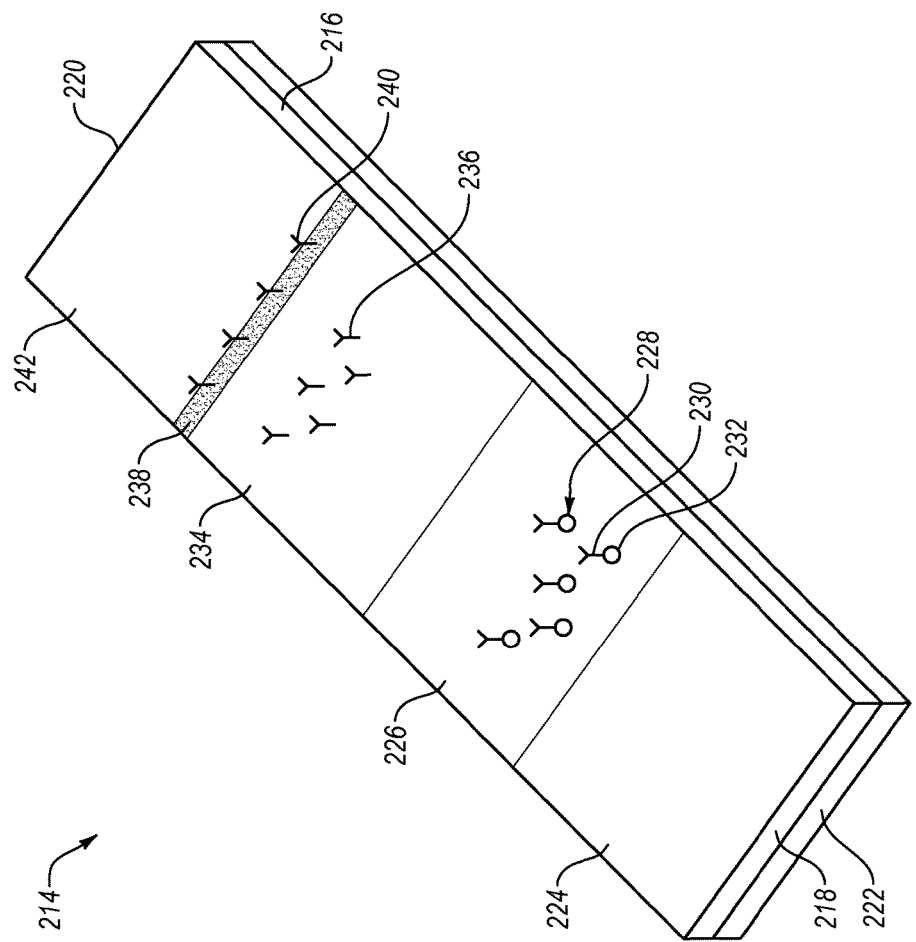
FIG. 2A is an isometric view of an LFA configured to be used with the photothermal spectroscopy assay reader of FIG. 1 according to an embodiment.

FIG. 2A is an isometric view of an embodiment of an LFA 214 configured to be read by any of the photothermal spectroscopy assay readers disclosed herein. However, it should be noted that any suitable LFA or other type of flow assay can be read by the photothermal spectroscopy assay readers disclosed herein. The LFA 214 can be used to determine a presence of one or more specific analytes in a sample using light 103 in the red range of the light spectrum. The LFA 214 can include a top layer 216 that functions as a capillary bed. In an embodiment, the top layer 216 can facilitate flow of fluid between a proximal end 218 and a distal end 220 of the LFA 2014. For example, the top layer 216 can include a porous material (e.g., matrix) having a thickness. The top layer 216 can at least partially include, by way of non-limiting example, porous paper, glass fibers, (e.g., a glass fiber mat or pad), polymers (e.g., carbonized polymers), or any other material capable of capillary action effective to induce lateral flow therethrough. For example, the top layer 216 an include nitrocellulose (e.g., a nitrocellulose or cellulose acetate paper or pad). The top layer 216 can be structurally supported by a support layer 222.

The top layer 216 exhibits a length and a width. The length, as measured from the proximal end 218 to the distal end 220, can be at least about 0.25 inches, such as about 0.5 inches to about 5 inches, about 1 inch to about 4 inches, about 1.5 inches to about 3 inches, about 0.5 inches to about 2 inches, about 0.5 inches, about 1 inches, about 1.5 inches, about 2 inches, about 2.5 inches, about 3 inches, or about 4 inches. The width (i.e., the distance measured perpendicular to the length) can be at least about 0.125 inches, such as about 0.25 inches to about 1 inch, about 0.375 inches to about 0.75 inches, about 0.5 inches to about 0.625 inches, about 0.25 inches to about 0.75 inches, or about 1 inch. In an embodiment, the top layer 216 can exhibit a ratio of length to width of about 1:1, or greater, such as about 1:1 to about 20:1, about 2:1 to about 10:1, about 3:1 to about 8:1, about 4:1 to about 6:1, about 2:1, about 3:1, about 4:1, or about 5:1.

The top layer 216 of the LFA 214 can include a sample pad 224 that is configured to receive a sample. The sample pad 224 can be positioned near the proximate end 218 of the top layer 216. In an embodiment, the sample pad 224 can be configured to receive a liquid sample, such as blood, plasma, urine, saliva, sweat or other liquid from an animal. In an embodiment, the sample pad 224 can be configured to receive a biological sample, chemical sample, environmental sample, food sample or similar sample. The sample can be processed prior to being applied to the sample pad 224. For example, the sample can be concentrated, isolated, or diluted. The sample can be introduced to the sample pad 224 via one or more of immersion, blotting, spotting, or any other suitable sampling technique.

The top layer 216 of the LFA 214 can include a conjugate pad 226 positioned adjacent to the sample pad 224 nearer the distal end 220 of the top layer 216. In an embodiment, the conjugate pad 226 can overlap the sample pad 224. The conjugate pad 226 includes a conjugate material 228 embedded or otherwise dispersed therein. The conjugate material 228 can be formulated to react with a specific analyte (e.g., antigen, molecule, etc.) to yield a specific conjugated analyte. The conjugate material 228 can include analyte binding molecules 230 conjugated to thermally-responsive indicator particles 232. Typically, the analyte binding molecules 230 can include chemical reactants, antibodies, antigens, bioactive agents, sugars, salts, collection materials, and other materials formulated to ensure satisfactory reaction, binding or bonding between the analyte and one or more indicator particles 232. For example, the analyte can be a virus and the analyte binding molecule 230 can contain the antibody or antigen to the virus.

The thermally-response indicator particles 232 of the conjugate materials 228 can be configured to absorb more energy from the light 103 (FIG. 1) in the red range of the light spectrum from the light source 102 (FIG. 1) than the sample and the top layer 216. For example, the thermally-response indicator particles 232 can be configured to absorb 1.25 times more energy from the light in the red range of the light spectrum than the sample and the top layer 216 (e.g., 2 times more energy, about 5 times more energy, about 10 times more energy, or more than 10 times more energy than the sample and the top layer 216).

The thermally-response indicator particles 232 can include at least one of blue cellulose nanobeads, silver nanoplates, silver nanoparticles, gold nanorods, gold nanocages, gold nanorods, gold nanocages, off-resonance gold nanospheres, multi-walled carbon nanotubes, carbon fullerenes, platinum nanoparticles, colloidal magnetite nanoparticles, ferrite nanoparticles, or conjugated dyes. The thermally-response indicator particles 232 can exhibit an average particle size of about 30 nm to about 500 nm (e.g., about 30 nm to about 100 nm, about 100 nm to about 250 nm, 250 nm to about 500 nm, or about 300 nm). For example, the thermally-response indicator particles 232 can include at least one of blue cellulose nanobeads, silver nanoplates, gold nanorods, or gold nanocages. In an embodiment, the sample can include blood (e.g., hemoglobin) and the thermally-response indicator particles 232 can include gold nanoparticles having an average particle size of about 40 nm.

In an embodiment, one or more conjugate materials 228 can be disposed or distributed across the width of the conjugate pad 226 in one or more lines, (e.g., stripe, or strip), dots, blocks, shapes, groups, or other designs. In an embodiment, the conjugate pad 226 can be configured to allow sufficient time for the sample and the one or more conjugate materials 228 to react together.

The top layer 216 of the LFA 214 includes a test region 234 that is located closer to the distal end 220 of the LFA 214 than the conjugate pad 226. In an embodiment, one or more collection materials 236 can be disposed in or on the test region 234. The one or more collection materials 236 an be disposed across the width of the top layer 216 in one or more lines (e.g., stripe, or strip), dots, blocks, shapes, groups, or other designs. The one or more collection materials 236 can be formulated to react with a conjugated analyte. For example, the one or more collection materials 236 can include chemical reactants, antibodies, antigens, bio-active agents, sugars, salts, collection materials, or other materials formulated to ensure satisfactory reaction, binding or bonding between the analyte and one or more collection materials 236. The one or more collection materials 236 can be configured to absorb less light than the thermally-response indicator particles 232. The test region 234 can include two or more regions including the one or more collection materials 236 to thereby allowing the photothermal spectroscopy assay reader 100 to test multiple regions of the LFA 214. For example, the two or more regions including the one or more collection materials 236 can be configured to react with different conjugated analytes.

In an embodiment, the LFA 214 can further include a control portion or control line 238 configured to provide a visual or thermal indication that the LFA 214 operated properly. The control line 238 can be disposed on a discrete portion of the top layer 216, on the test region 234 or proximate to the distal end 220 (e.g., closer to the distal end 220 than the test region 234). The control line 238 can include a molecule or group of molecules 240 located in a discrete portion of the top layer 216. The molecules 240 in the control line 238 can be configured to react with unreacted conjugate materials 236 or the sample (e.g., any substance in the sample fluid or carried therewith) in order to demonstrate that the LFA 214 worked properly or is complete.

In an embodiment, the top layer 216 can include one or more storage portions 242. The one or more storage portions 242 can be configured as pads, reservoirs, or portions of the top layer 216 configure to store a large volume of the sample compared to other portions of the top layer 216. For example, the LFA 214 can include a storage portion near the proximal end 218 configured to hold a large volume of the sample fluid applied to the sample pad 224. The top layer 216 can then draw the sample therefrom, such as the sample travels through the top layer 216 by capillary action. A similar storage portion 242 can be located near the distal end 220 and can be configured to wick the sample therein, thereby drawing or allowing a sufficient amount of the sample to travel to the distal end 220 to ensure the test provides accurate results.

Figure 2B:
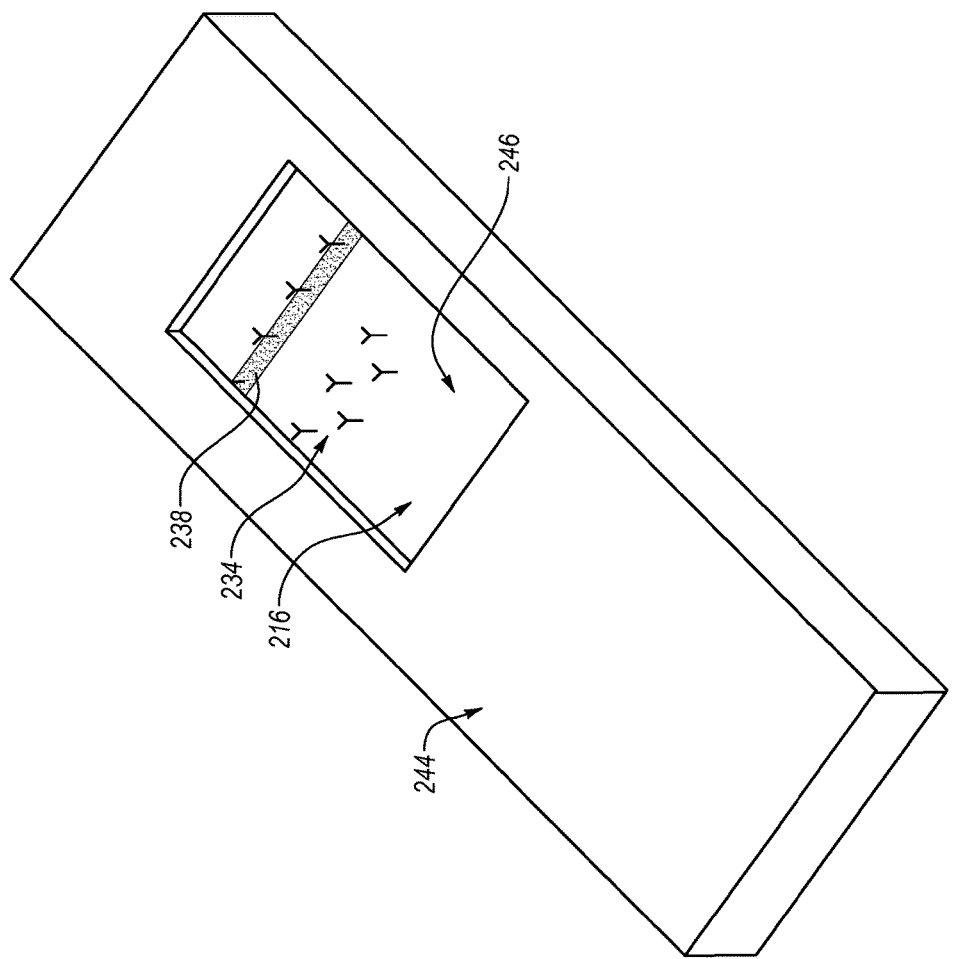
FIG. 2B is an isometric view of an LFA including a housing and configured to be used with the photothermal spectroscopy assay reader of FIG. 1 according to an embodiment.

In an embodiment shown in FIG. 2B, the LFA 214 can include a housing 244 that at least partially or substantially encloses the top layer 216 including the sample pad 224, the conjugate pad 226, the test region 234, the control line 238 and the storage portion 242. The housing 244 can include one or more openings 246 (e.g., a cutout, view hole, or window), above the test region 234 or the control line 238. For example, the one or more openings 246 can be configured to allow light in the red range of the light spectrum to illuminate and be received by at least a portion of the test region 234 and allow a thermal response from the test region 234 to be detected by a thermal sensor such as the thermal sensor 110 (FIG. 1). For example, the one or more openings 246 can be covered with a material that is transparent to a light in the red range of the spectrum and a thermal response. In an embodiment, the one or more openings 246 can be covered with a transparent material (e.g., glass, plastic or the like) to allow a user to visibly inspect the top layer 216. The housing 244 can additionally include a sample opening (not shown) through which a sample can be introduced to the sample pad 224. In an embodiment, the top layer 216 can protrude out of the sample opening to or beyond the outer periphery of the housing 244.

Figure 2C:
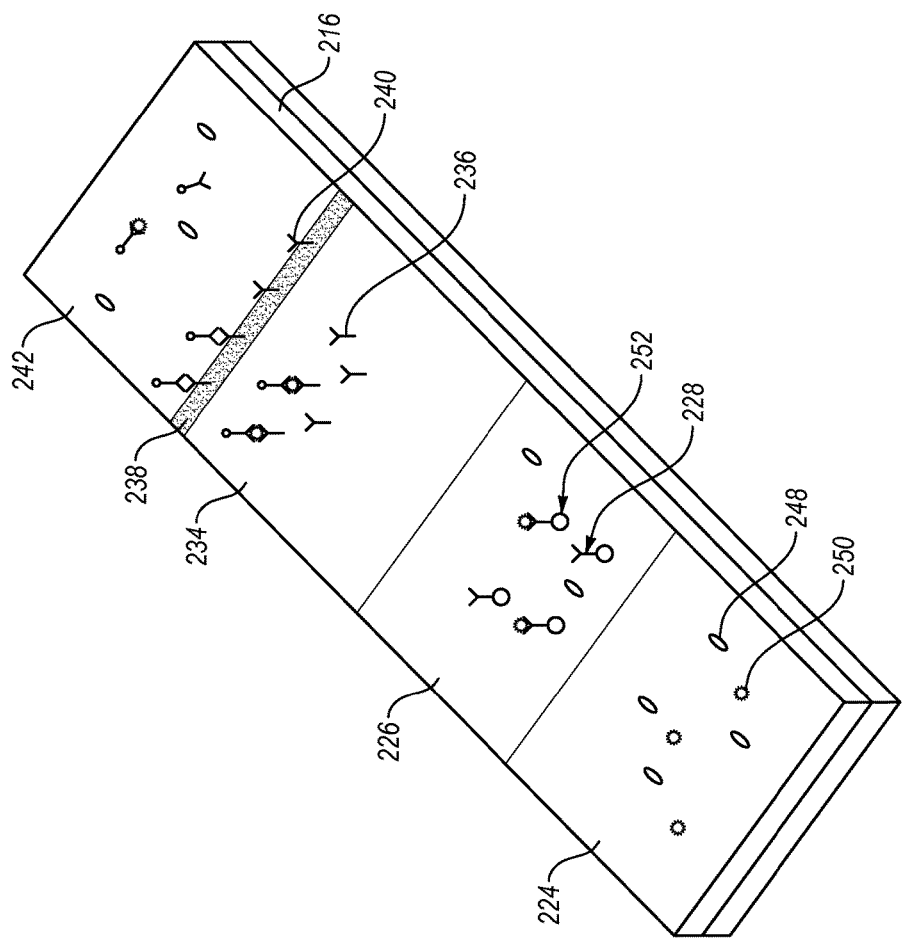
FIG. 2C is an isometric schematic view of a sample traveling through the LFA shown in FIG. 2A according to an embodiment.

FIG. 2C is an isometric schematic illustration of a sample 248 including an analyte 250 traveling through the top layer 216 of the LFA 214 according to an embodiment. As previously discussed, the top layer 216 can be formed of a porous material that facilitates transport of the sample 248 through the LFA 214 via capillary action. In use, the sample 248 including the analyte 250 can be applied to the sample pad 224. The porous top layer 216 transports the sample 248 including the analyte 250 therein from the sample pad 224 to the conjugate pad 226. When the sample 248 enters the conjugate pad 226, at least some of the analyte 250 begins to bind with at least some of the conjugate material 228 to form a conjugated analyte 252.

The sample 248 can then flow laterally through the test region 234 and at least some of the conjugated analyte 252 can bind with the one or more collection materials 236. For example, the one or more collection materials 236 can bind the conjugated analyte 252 to the test region 234 of the top layer 216. The one or more collection materials 236 can bind a sufficient number of the conjugated analyte 252 that the photothermal spectroscopy assay reader can detect the presence of the conjugate material 228. The photothermal spectroscopy assay reader can detect relatively low concentrations of the conjugate material 228 due to the high energy absorbance of the conjugate material 228 relative to the sample 248 and the top layer 216.

The sample 248 can then flow laterally through the control line 238 and into the storage portion 242 of the top layer 216. For example, the control line 238 can include one or more molecules 240 configured to react with the sample 248 to indicate that the LFA 214 functioned correctly. For example the control line 238 can provide a visual and/or thermal indication that the LFA 214 worked correctly.

Figure 3:
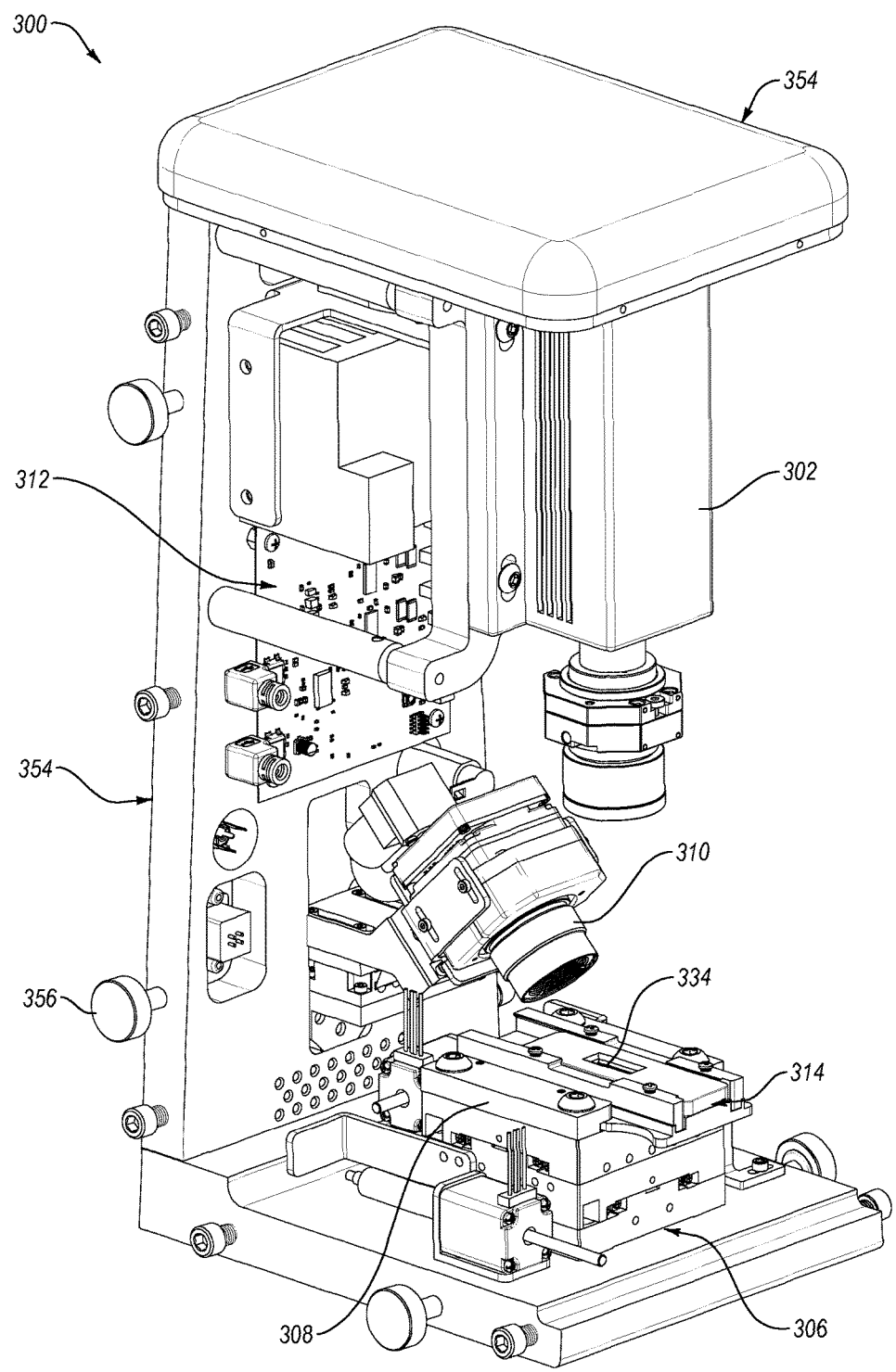
FIG. 3 is an isometric view of a photothermal spectroscopy assay reader according to an embodiment.

FIG. 3 is an isometric view of a tabletop photothermal spectroscopy assay reader 300 according to a more detailed embodiment. The photothermal spectroscopy assay reader 300 includes a light source 302 that is configured to emit a light that is in the red range of the spectrum (e.g., about 600 nm to about 750 nm) towards a test region 334 of an LFA 314. For example, the light source 302 can include any of the light sources previously discussed with respect to the light source 102 shown in FIG. 1. The photothermal spectroscopy assay reader 300 can include a sample holder 306 having a positioning feature 308 (e.g., a channel). The photothermal spectroscopy assay reader 300 can further include a thermal sensor 310 configured to detect a thermal response from the LFA 314 that is communicably and operably coupled to computer 312. For example, the thermal sensor 310 can include any of the thermal sensors previously discussed with respect to the thermal sensor 110 shown in FIG. 1.

The photothermal spectroscopy assay reader 300 further includes a support structure 354. The light source 302, the sample holder 306, and the thermal sensor 310 can be attached or supported by the support structure 354. The computer 312 can also be attached or supported by the support structure 354 or can be located remote from the support structure 354.

The support structure 354 can further include one or more components that allow individual components of the photothermal spectroscopy assay reader 300 to be moveable. For example, the support structure 354 can include one or more knobs 356 that can allow a user to move individual components of the photothermal spectroscopy assay reader 300 along a slideable guideway. In an embodiment, the one or more knobs 356 can enable the user to operably move the light source 302, the sample holder 306, or the thermal sensor 310 via a carriage or other moveable structure. For example, the user can use the one or more knobs 356 to calibrate the photothermal spectroscopy assay reader 300 such that light emitted by the light source 302 is directed towards the test region of the LFA 314 and the thermal sensor 310 detects the thermal response of the LFA 314. In an embodiment, the one or more knobs 356 can allow the user to move the light source 302 such that light emitted therefrom can be emitted towards two or more different regions of the LFA 314. In an embodiment, moving the sample holder 306 can allow a user to insert the LFA 314 onto the sample holder 306.

The support structure 354 can further include components that enable the removal or replacement of specific components. In an embodiment, the support structure 354 can include components to remove or replace the light source 302. For example, removing and replacing the light source 302 can allow the photothermal spectroscopy assay reader 300 to have a specific type of light source 302 (e.g., LED light source, or a pulse laser) or a light source 302 that emits a specific wavelength.

The photothermal spectroscopy assay reader 300 can be modified in a variety of ways. In an embodiment, the photothermal spectroscopy assay reader 300 can be modified to include a covering that covers at least a portion of the photothermal spectroscopy assay reader 300. For example, individual components of the photothermal spectroscopy assay reader 300 can be enclosed by the covering. In such an embodiment, a housing can include an opening to insert and retrieve the LFA 314. In an embodiment, the photothermal spectroscopy assay reader 300 can include a display and an input device, such as a keyboard or mouse. In an embodiment, the photothermal spectroscopy assay reader 300 does not include the support structure 354. For example, the individual components of the photothermal spectroscopy assay reader 300 can be positioned using other means, such as manual positioning and aligning. In an embodiment, the photothermal spectroscopy assay reader 300 can be modified to be a handheld or portable unit.

Figure 4:
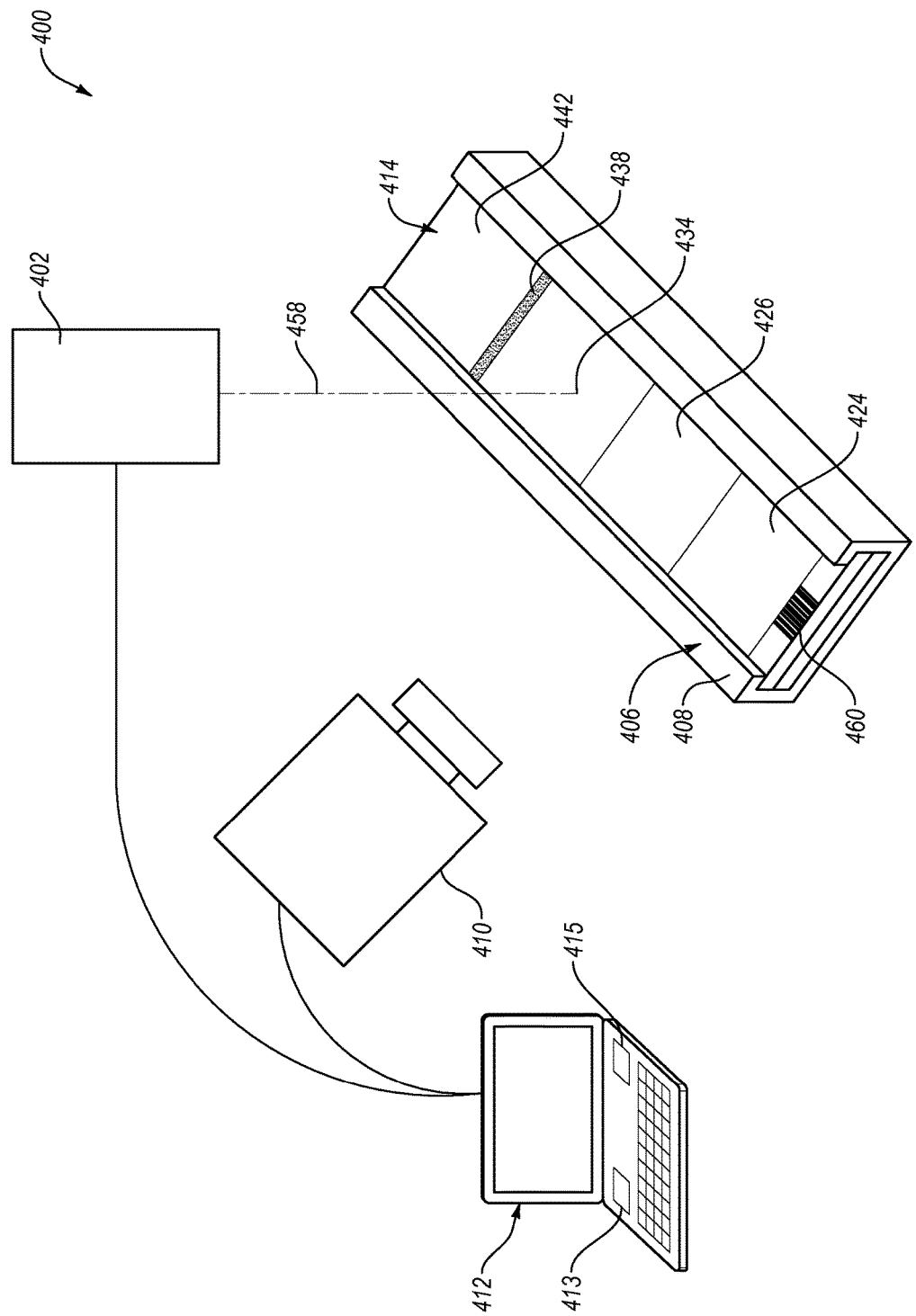
FIG. 4 is an isometric schematic view of a method of detecting a presence of an analyte in a sample using a photothermal spectroscopy assay reader according to an embodiment.

FIG. 4 is an isometric schematic view of a method of detecting an analyte using a photothermal spectroscopy assay reader 400 or any photothermal spectroscopy assay reader disclosed herein according to an embodiment. In an embodiment, the photothermal spectroscopy assay reader 400 receives one or more signals indicating that an LFA 414 is present on the sample holder 406. The photothermal spectroscopy assay reader 400 can receive the one or more signals from sensors positioned on the sample holder 406, sensors spaced from the sample holder 405 (e.g., a light sensor), input received from a user or from another source. In an embodiment, the one or more signals are sent to a computer.

After receiving the one or more signals, the photothermal spectroscopy assay reader 400 can instruct the light source 402 to emit light, such as a laser beam 458, towards the test region 434 of the LFA 414. The light source 402 can emit light having an average wavelength of about 600 nm to about 750 nm. The light source 402 can include any of the light source disclosed herein. The light source 402 can emit light in response to receiving the one or more signals. In an embodiment, the light source 402 can emit light in response to a program run by the photothermal spectroscopy assay reader 400 or in response to input received from a user. The light source 402 can expose at least a portion of the test region 434 of the LFA 414 to light.

The photothermal spectroscopy assay reader 400 can detect at least a portion of the thermal response from the test region 434 of the LFA 414 responsive to emitting light from the light source 402. The photothermal spectroscopy assay reader 400 detects the thermal response using a thermal sensor 410. The thermal sensor 410 can be configured to detect the thermal response while the light is emitted, immediately after the light is emitted, at some period of time after the light is emitted, or at some other interval. For example, the light source 402 can be configured to emit a pulse laser beam 458 every 6 ms, while the thermal sensor 410 can be configured to detect the thermal response every 7 ms. Such a configuration can maximize the likelihood that the thermal sensor 410 detects the maximum temperature gradient.

Figure 5:
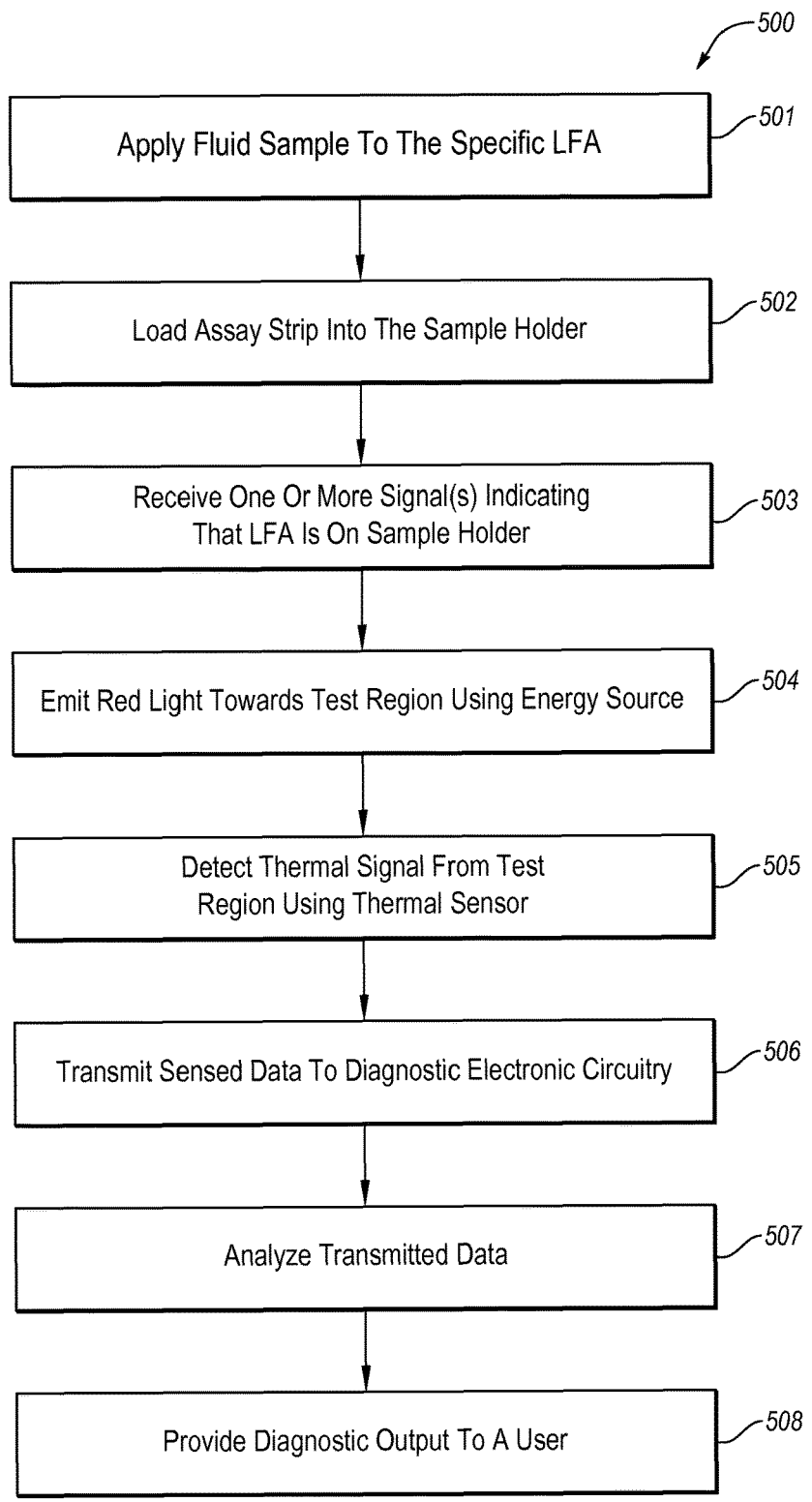
FIG. 5 is a flow diagram of an embodiment of a method of detecting an analyte in a sample using any of the photothermal spectroscopy assay readers disclosed herein.

FIG. 5 is a flow diagram of the method illustrated in FIG. 4 according to an embodiment. It should be noted that the LFA and the photothermal spectroscopy assay reader 400 can be configured according to any of the embodiments disclosed herein.

In act 501, a fluid sample is applied to a specific LFA 414 that is configured to detect one or more specific analytes within a specific sample. For example, the LFA 414 can be configured to detect one or more analytes within a blood sample. The sample can be applied to a sample pad 424 of the LFA 414. As discussed in more detail in FIGS. 2A and 2B, the sample flows laterally through the LFA 414 via capillary action. If the sample includes one or more specific analytes, some of the one or more analytes can react with a conjugate material within the conjugate pad to form a conjugated analyte. The sample and the conjugated analyte can flow through the test region 434 of the LFA 414. Some of the conjugated analytes can react with one or more collection materials. Additionally, the sample can react with the control line 438

In act 502, the LFA 414 can be loaded into a sample holder 406 of the photothermal spectroscopy assay reader 400. The LFA 414 can be loaded into the sample holder 406 immediately after the sample is applied to the LFA 414, before the sample is applied to the LFA 414, or at some time thereafter. The LFA 414 can be positioned on the sample holder 406 using a positioning feature 408. The positioning feature 408 can include a channel or bracket that secures the LFA 414 and positions the LFA 414.

The LFA 414 can include one or more identification markers 460 thereon that allows the user or the photothermal spectroscopy assay reader 400 to identify the specific type of LFA 414 selected. For example, identification markers 460 of the LFA 414 can include numbers, letters, symbols, color combinations, bar-codes, magnetic strips, or other identification markers that can be used by the user and/or the photothermal spectroscopy assay reader 400 to identify the LFA 414. For example, the LFA 414 can include a bar-code or a magnetic strip. The photothermal spectroscopy assay reader 400 can include a component that identifies the specific LFA 414 when the LFA 414 is loaded into the sample holder 406. For example, the photothermal spectroscopy assay reader 400 can include a reader (e.g., an optical bar-code reader or magnetic reader) configured to determine the type of sample, the type of analyte being tested, the conjugate material, or other information related to the LFA 414 from the one or more identification markers 460. The photothermal spectroscopy assay reader 400 can use the information to determine the test procedures (e.g., wavelength of light to be used, light intensity) to be used. For example, detecting the one or more identification markers can cause computer 412 operably coupled to the photothermal spectroscopy assay reader 400 to select one or more test procedures stored in memory electrical circuitry 413 of the computer 412. Alternatively, detecting the one or more identification markers 460 can cause the computer 412 to display specific information to the user, such as recommended procedures or relative absorbance of the materials present in the LFA 414.

In act 503, the computer 412 receives one or more signals indicating that the LFA 414 is present on the sample holder 406. In an embodiment, the sample holder 406 can include one or more sensors that detect a presence or a position of the LFA 414 on the sample holder 406. In an embodiment, the computer 412 can receive the one or more signals indicating the presence of the LFA 414 on the sample holder 406 using other techniques. For example, a user can communicate to the photothermal spectroscopy assay reader 400 that the LFA 414 is on the sample holder 406 using an input. In an embodiment, the photothermal spectroscopy assay reader 400 can receive the one or more signals from a device configured to detect the one or more identification markers 460 or from the light sensor 104 shown in FIG. 1.

In act 504, the light source 402 of the photothermal spectroscopy assay reader 400 emits light in the red range of the light spectrum towards the test region 434 of the LFA 414. The light source 402 can include any of the light sources disclosed herein. In an embodiment, the light source 402 is configured to emit the laser beam 458 towards the LFA 414 after receiving the one or more signals indicating that the LFA 414 is present on the sample holder 406. The emitted light can be directed at one or more locations of the test region 434 or the control line 438.

In act 505, the thermal sensor 410 can detect the thermal response from the test region 434 of the LFA 414 responsive to the test region 434 being irradiated by the light from the light source 402. The thermal sensor 410 can be configured to detect the thermal response while the light is emitted, immediately after the light is emitted, at some period of time after the light is emitted, or at some other interval.

In act 506, the one or more thermal sensors 410 transmit data to diagnostic electrical circuitry 415 of the computer 412. The data sent to the diagnostic electrical circuitry 415 can be the raw data detected by the thermal sensor 410. Alternatively, the data sent by the thermal sensor 410 can be at least partially analyzed by the thermal sensor 410 or by another component. Additionally, the data transmitted by the thermal sensor 410 can include additional information. For example, the data transmitted can include information related to the LFA 414, the light emitted by the light source 402, or other data. In an embodiment, at least some of the data can be sent to the diagnostic electrical circuitry 415 can be transmitted from other components of the photothermal spectroscopy assay reader 400 (e.g., the light source 402). Alternatively, some of the data can be sent to an intermediary (e.g., analog-to-digital circuitry) before being received by the diagnostic electrical circuitry 415.

The thermal sensor 410 can transmit the data using any suitable technique. In an embodiment, the thermal sensor 410 can be wiredly connected to the diagnostic electrical circuitry 415. In an embodiment, the thermal sensor 410 can be wirelessly connected to the diagnostic electrical circuitry 415 using WIFI, Bluetooth, or other wireless communication means.

In act 507, the diagnostic electrical circuitry 415 analyzes the data transmitted by the thermal sensor 410. In an embodiment, the diagnostic electrical circuitry 415 can analyze the temperature gradient of the thermal response. For example, the diagnostic electrical circuitry 415 can analyze the profile of the temperature gradient. In an embodiment, the diagnostic electrical circuitry 415 can compare the expected thermal response if the analyte is not present in the sample with the detected thermal response. The expected thermal response can be calculated or stored in memory. The diagnostic electrical circuitry 415 can analyze the data to determine whether the analyte is present or can quantitatively determine the amount of analyte present in the sample. For example, the diagnostic electrical circuitry 415 can use relative difference between the expected thermal response and the detected thermal response to determine the amount of conjugate material in the test region 434, which can be correlated to the amount of analyte within the sample such as concentration in the sample.

In act 508, the diagnostic electrical circuitry 415 transmits to the user the diagnostic condition. The diagnostic condition can contain at least one result from the analysis performed in act 507. For example, the diagnostic condition can simply contain a "pass/fail result" relating to the presence of the analyte. In an embodiment, the diagnostic condition can include the quantitative amount of analyte present within the sample based on the detected thermal response, such as concentration. The diagnostic condition can include additional information about the test. For example, the diagnostic condition can include information related to the wavelength of the light, the intensity of the light, the type of LFA 414 used, the type of sample tested, the conjugate material used, and/or other information related to the test. The diagnostic electrical circuitry 415 transmits the diagnostic condition to a user. The diagnostic electrical circuitry 415 can transmit the diagnostic condition wirelessly or wiredly.

The reader will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. The reader will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. The reader will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the reader will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, the various embodiments described herein can be implemented, individually and/or collectively, by various types of electro-mechanical systems having a wide range of electrical components such as hardware, software, firmware, or virtually any combination thereof; and a wide range of components that may impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs. Those skilled in the art will also appreciate that examples of electro-mechanical systems include but are not limited to a variety of consumer electrical systems, as well as other systems such as motorized transport systems, factory automation systems, security systems, and communication/computing systems. Those skilled in the art will recognize that electro-mechanical as used herein is not necessarily limited to a system that has both electrical and mechanical actuation except as context may dictate otherwise.

In a general sense, the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). The subject matter described herein may be implemented in an analog or digital fashion or some combination thereof.

The herein described components (e.g., steps), devices, and objects and the discussion accompanying them are used as examples for the sake of conceptual clarity. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural and/or singular terms herein, the reader can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

In some instances, one or more components may be referred to herein as "configured to." The reader will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense the convention (e.g., "a system having at least one of A, B, or C" would include but not be limited to systems that have A alone, B alone, C alone, A and B together, A and C together, B and C together, and/or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

With respect to the appended claims, the recited operations therein may generally be performed in any order. Examples of such alternate orderings may include overlapping, interleaved, interrupted, reordered, incremental, preparatory, supplemental, simultaneous, reverse, or other variant orderings, unless context dictates otherwise. With respect to context, even terms like "responsive to," "related to or other past-tense adjectives are generally not intended to exclude such variants, unless context dictates otherwise.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A photothermal spectroscopy assay reader for detecting a presence of an analyte in a sample disposed in a lateral flow assay, the photothermal spectroscopy assay reader comprising:
    a sample holder configured to receive a lateral flow assay having a test region;
    at least one lateral flow assay disposed on the sample holder, the at least one lateral flow assay including:
        a sample pad configured to receive a sample;
        a conjugate pad including a conjugate material, wherein the conjugate material is configured to bind to a selected analyte when the selected analyte is present in the sample, and the conjugate material is selected to absorb more energy from a light source emitting light exhibiting an average wavelength of about 600 nm to about 750 nm than the sample when the lateral flow assay is exposed to the light, the conjugate material including thermally-responsive indicator nanoparticles, the thermally responsive nanoparticles including cellulose nanobeads; and a test region including a collection material and a top layer of the lateral flow assay;

at least one light source configured to emit light having an average wavelength of about 600 nm to about 750 nm to be received by the test region of the lateral flow assay; and at least one thermal sensor configured to detect at least a thermal gradient from the test region of the lateral flow assay;

wherein the thermally-responsive indicator nanoparticles absorb at least 1.25 times more energy than the sample and a top layer of the lateral flow assay.

2. The photothermal spectroscopy assay reader of claim 1, wherein the light source is configured to emit the light with an average wavelength of about 600 nm to about 650 nm.

3. The photothermal spectroscopy assay reader of claim 1, wherein the light source is configured to emit the light with an average wavelength of about 600 nm to about 700 nm.

4. The photothermal spectroscopy assay reader of claim 1 wherein the light source includes a laser configured to emit a laser beam with the average wavelength of about 600 nm to about 750 nm.

5. The photothermal spectroscopy assay reader of claim 4 wherein the laser includes a pulse laser configured to emit the laser beam.

6. The photothermal spectroscopy assay reader of claim 5 wherein the pulse laser is configured to emit the laser beam at about every 1 ms to about every 1000 ms.

7. The photothermal spectroscopy assay reader of claim 1 wherein the at least one thermal sensor includes at least one infrared camera.

8. The photothermal spectroscopy assay reader of claim 1, further including:

diagnostic electrical circuitry coupled to the at least one thermal sensor;

wherein the at least one thermal sensor is configured to output one or more signals including information related to a detected thermal response; and wherein the diagnostic electrical circuitry is further configured to provide a diagnostic condition at least partially based on the one or more signals output by the at least one thermal sensor.

9. The photothermal spectroscopy assay reader of claim 8 wherein the diagnostic condition includes an indication of the presence of the analyte within the sample introduced to the lateral flow assay.

10. A method of using a photothermal spectroscopy assay reader to determine a presence of an analyte in a lateral flow assay, the method comprising:

receiving one or more signals indicating the lateral flow assay is present in a sample holder of the photothermal spectroscopy assay reader, wherein the lateral flow assay includes a test region and thermally-responsive indicator nanoparticles, the thermally-responsive indicator nanoparticles including cellulose nanobeads;

emitting light from a light source that is received by the test region of the lateral flow assay, wherein the light exhibits an average wavelength of about 600 nm to about 750 nm; and responsive to emitting the light, detecting, with a thermal sensor, at least a thermal gradient from the test region of the lateral flow assay;

wherein the thermally-responsive indicator nanoparticles absorb at least 1.25 times more energy than the sample and a top layer of the lateral flow assay.

11. The method of claim 10, further including:

transmitting one or more signals from the thermal sensor to diagnostic electrical circuitry, wherein the one or more signals includes data detected by the thermal sensor; and analyzing the data with the diagnostic electrical circuitry to determine if the analyte is present within the lateral flow assay.

12. The method of claim 11, further including transmitting the analyzed data from the diagnostic electrical circuitry to a user.

13. The method of claim 11, wherein analyzing the data includes comparing an expected thermal response of the test region without the analyte present with the thermal response detected by the thermal sensor.

14. The method of claim 10, wherein the light source includes a laser configured to emit a laser beam with the average wavelength of about 600 nm to about 750 nm.

15. The method of claim 14, wherein the laser includes a pulse laser configured to emit the laser beam.

16. The method of claim 10, further including:

detecting an identification marker of the lateral flow assay; and identifying a conjugate material configured to bind to the analyte responsive to detecting the identification marker.

17. The method of claim 10 wherein the thermally-responsive indicator nanoparticles includes blue cellulose nanobeads.

18. The method of claim 10 wherein the thermally-responsive indicator nanoparticles includes gold nanoparticles.

19. The method of claim 10 wherein the thermally-responsive indicator nanoparticles includes gold nanoparticles exhibiting a particle size of about 30 nm to about 100 nm.

20. The method of claim 10 wherein the thermally-responsive indicator particles includes at least one of silver nanoplates, silver nanoparticles, gold nanorods, gold nanocages, gold nanorods, gold nanocages, off-resonance gold nanospheres, multi-walled carbon nanotubes, carbon fullerenes, platinum nanoparticles, colloidal magnetite nanoparticles, ferrite nanoparticles, or conjugated dyes.

21. An assay kit, comprising:

a lateral flow assay including, a sample pad configured to receive a sample;

a conjugate pad including a conjugate material, wherein the conjugate material is configured to bind to a selected analyte when the selected analyte is present in the sample, and the conjugate material is selected to absorb more energy from a light source emitting light exhibiting an average wavelength of about 600 nm to about 750 nm than the sample when the lateral flow assay is exposed to the light, the conjugate material including thermally-responsive indicator nanoparticles, the thermally responsive nanoparticles including cellulose nanobeads; and a test region including a collection material and a top layer of the lateral flow assay; and a photothermal spectroscopy assay reader including, a sample holder configured to receive the lateral flow assay;

the light source configured to emit the light exhibiting the average wavelength of about 600 nm to about 750 nm to be received by the test region of the lateral flow assay; and a thermal sensor positioned and configured to detect at least a temperature gradient from the test region of the lateral flow assay;

wherein the thermally-responsive indicator nanoparticles absorb at least 1.25 times more energy than the sample and a top layer of the lateral flow assay.

22. The assay kit of claim 21 wherein the thermally-responsive indicator nanoparticles includes gold nanoparticles exhibiting a particle size of about 30 nm to about 500 nm.

23. The assay kit of claim 21 wherein the conjugate material includes at least one of silver nanoplates, silver nanoparticles, gold nanorods, gold nanocages, gold nanorods, gold nanocages, off-resonance gold nanospheres, multi-walled carbon nanotubes, carbon fullerenes, platinum nanoparticles, colloidal magnetite nanoparticles, ferrite nanoparticles, or conjugated dyes.

24. The assay kit of claim 21 wherein the top layer of the lateral flow assay of the test region includes nitrocellulose.

25. The assay kit of claim 21 wherein the collection material and the top layer of the lateral flow assay of the test region are configured to absorb less energy from the light than the conjugate material.

26. The assay kit of claim 21 wherein the light source includes a laser configured to emit a laser beam having the average wavelength of about 600 nm to about 750 nm.

27. The assay kit of claim 26 wherein the laser includes a pulse laser configured to emit the laser beam.

28. The assay kit of claim 21 wherein the cellulose nanobeads includes blue cellulose nanobeads.

29. The photothermal spectroscopy assay reader of claim 1 wherein:

the at least one light source includes a plurality of light sources, the plurality of light sources including:
a first light source that emits the light towards a first location on the at least one lateral flow assay; and
a second light source that emits the light towards a second location on the at least one lateral flow assay that is different than the first location; and the at least one thermal sensor includes a plurality of thermal sensors, the plurality of thermal sensors including:
a first thermal sensor configured to detect a thermal response from the first location; and
a second thermal sensor configured to detected a thermal response from the second location.

* * * * *

UNITED STATES PATENT AND TRADEMARK OFFICE
CERTIFICATE OF CORRECTION

PATENT NO. : 10,094,823 B2
APPLICATION NO. : 14/604396
DATED : October 9, 2018
INVENTOR(S) : Matthew P. Horning et al.

Page 1 of 1

It is certified that error appears in the above-identified patent and that said Letters Patent is hereby corrected as shown below:

In the Claims

Column 23, Claim 23, Lines 21-22:
"nanoparticles, gold nanorods, gold nanocages, gold nanorods, gold nanocages, off-resonance gold nanospheres,"
Should read:
--nanoparticles, gold nanorods, gold nanocages, off-resonance gold nanospheres,--

Signed and Sealed this
Twenty-seventh Day of November, 2018

Andrei Iancu
*Director of the United States Patent and Trademark Office*